US009217172B2

United States Patent
Johnson et al.

(10) Patent No.: US 9,217,172 B2
(45) Date of Patent: Dec. 22, 2015

(54) COMPOSITIONS AND METHODS FOR TOXIGENICITY TESTING

(71) Applicant: CELLSNAP, LLC, Madison, WI (US)

(72) Inventors: Eric Arthur Johnson, Madison, WI (US); Sabine Pellett, Madison, WI (US); William Howard Tepp, Stoughton, WI (US); Regina Clare Meyer Whitemarsh, Madison, WI (US)

(73) Assignee: CELLSNAP, LLC, Madison, WI (US)

( * ) Notice: Subject to any disclaimer, the term of this patent is extended or adjusted under 35 U.S.C. 154(b) by 0 days.

(21) Appl. No.: 14/347,074

(22) PCT Filed: Sep. 28, 2012

(86) PCT No.: PCT/US2012/057825
§ 371 (c)(1),
(2) Date: Mar. 25, 2014

(87) PCT Pub. No.: WO2013/049508
PCT Pub. Date: Apr. 4, 2013

(65) Prior Publication Data
US 2014/0234857 A1    Aug. 21, 2014

Related U.S. Application Data

(60) Provisional application No. 61/540,693, filed on Sep. 29, 2011.

(51) Int. Cl.
| | |
|---|---|
| *C12N 5/078* | (2010.01) |
| *C12N 5/079* | (2010.01) |
| *C12Q 1/37* | (2006.01) |
| *G01N 33/50* | (2006.01) |

(52) U.S. Cl.
CPC .............. *C12Q 1/37* (2013.01); *G01N 33/5073* (2013.01); *G01N 2333/33* (2013.01)

(58) Field of Classification Search
CPC ....... C12N 5/079; C12N 5/078; C12N 5/0696
USPC ......................................................... 435/366
See application file for complete search history.

(56) References Cited

U.S. PATENT DOCUMENTS

| | | | |
|---|---|---|---|
| 7,229,605 B2 | 6/2007 | Holland et al. | |
| 8,198,034 B2 | 6/2012 | Fernandez-Salas | |

(Continued)

FOREIGN PATENT DOCUMENTS

| | | |
|---|---|---|
| EP | 1597584 | 2/2004 |
| EP | 2015065 | 4/2006 |

(Continued)

OTHER PUBLICATIONS

Hester, Mark E. et al, Molecular Therapy, vol. 19(10) pp. 1905-1912, Oct. 2011.*

(Continued)

*Primary Examiner* — Albert Navarro
*Assistant Examiner* — Ginny Portner
(74) *Attorney, Agent, or Firm* — Hueschen and Sage

(57) ABSTRACT

The present invention relates to compositions and methods for testing agents (e.g., *Clostridium botulinum* neurotoxin (BoNT) detection and analysis). In particular, the present invention relates to the use of Human induced pluripotent stem (hiPS) derived cells for agent detection and analysis.

22 Claims, 6 Drawing Sheets

(56) References Cited

U.S. PATENT DOCUMENTS

| | | | | |
|---|---|---|---|---|
| 8,420,352 | B2* | 4/2013 | Oyler | C07K 14/33 435/252.7 |
| 8,609,413 | B2* | 12/2013 | Suter et al. | 435/377 |
| 8,778,623 | B2* | 7/2014 | Johnson | C12Q 1/37 435/326 |
| 9,102,901 | B2* | 8/2015 | Wang | C11D 3/046 |
| 2003/0032891 | A1 | 2/2003 | Jenkins | |
| 2010/0167286 | A1* | 7/2010 | Reijo Pera et al. | 435/6 |
| 2010/0216181 | A1* | 8/2010 | Daigh et al. | 435/29 |
| 2010/0233802 | A1 | 9/2010 | Zhu | |
| 2010/0279403 | A1* | 11/2010 | Rajesh et al. | 435/366 |
| 2011/0008397 | A1* | 1/2011 | Cohen | 424/400 |
| 2011/0046092 | A1* | 2/2011 | Suter et al. | 514/150 |
| 2011/0053244 | A1* | 3/2011 | Oyler et al. | 435/188 |
| 2012/0276063 | A1* | 11/2012 | Meyer et al. | 424/93.7 |
| 2014/0248644 | A1* | 9/2014 | Wang | C12Q 1/37 435/7.94 |
| 2015/0044709 | A1* | 2/2015 | Eisele | 435/8 |

FOREIGN PATENT DOCUMENTS

| | | | |
|---|---|---|---|
| EP | 1926744 | | 4/2010 |
| GB | 2398636 | | 8/2004 |
| GB | 2416849 | | 2/2006 |
| WO | WO 9533850 | | 12/1995 |
| WO | WO2004031773 | | 4/2004 |
| WO | WO 2005/076785 | | 8/2005 |
| WO | 2009/076529 | * | 6/2009 ............... C12N 5/06 |
| WO | WO 2009/114748 | | 9/2009 |
| WO | 2010/099539 | * | 9/2010 |
| WO | WO2010105234 | | 9/2010 |
| WO | WO2011025852 | | 3/2011 |
| WO | WO2011056971 | | 5/2011 |
| WO | WO 2012/123370 | | 9/2012 |
| WO | WO2012135621 | | 10/2012 |

OTHER PUBLICATIONS

Berntsson, Ronnie P.A. et al, Structure of dual receptor binding to botulinum neurotoxin B, Nature Communication, 2013, vol. 4,(2058), pp. 1-13.*

Whitemarsh, Regina C. M. et al, Toxicological Sciences, vol. 126(2), pp. 426-435, 2012, Novel Applicaton of Human Neurons Derived from Induced Pluripotent Stem Cells for Highly Sensitive Botulinum Neurotoxin Detection.*

McNutt, Patrick et al, Cell Based Assay for Neurotoxins, Chapter 12, pp. 247-271, Springer Science+Business Media Dordrecht, 2015, P. Gopalakrishnakone et al (eds) Biological Toxins and Bioterrorism, Toxicology.*

Jacky, Birgitte P. S. et al, PLOS Pathogens, May 2013, vol. 9(5) e1003369, pp. 1-17, Identification of Fibroblast Growth Factor Receptor 3 (FGFR3) as a Protein Receptor for Botulinum Neurotoxin Serotype A (BoNT/A).*

Takahashi, K et al, Cell, vol. 131, Nov. 30, 2007, pp. 861-872, Induction of Pluripotent Stem Cells from Adult Human Fibroblasts by Defined Factors.*

International Search Report and Written Opinion for PCT/US2012/057825 of Nov. 8, 2012.

Karumbayaram, et al., Stem Cells, vol. 27, No. 4, p. 806-811, 2009.

Kiris, et al., Stem Cell Res., vol. 6, No. 3, p. 195-205, May 2011.

Pellett, et al., FEBS Lett., vol. 581, No. 25, p. 4803-4808, 2007.

Chang et al., Naunyn-Schmiedeberg's Arch. Pharmacol. vol. 282, p. 129-142 (1974).

Göschel et al., Exp. Neurol., vol. 147, p. 1, 1997.

International Search Report With Writtent Opinion for PCT/EP2010/006967 of Jan. 24, 2011.

International Search Report for PCT/EP2013/074276 of Feb. 13, 2014.

James et al., Am. J. Physiol. Gastrointest. Liver Physiol. vol. 285, p. G291-G297 (2003).

Keller J., et al., Biochemistry, vol. 43, No. 2, p. 526-532, Jan. 20, 2004.

Pearce L. Bruce, et al., Toxicon Elmsford, vol. 35, No. 9, p. 1373-1412, Sep. 1, 1997.

Pellett, et al., Journal of Pharmacological and Toxicological Methods, vol. 61, No. 3, p. 304-310, May 1, 2010.

Pellizzari, R., et al., Toxicology Letters, vol. 102-103, p. 191-197, Dec. 28, 1998.

Purkiss, et al. Clostridium botulinum Neurotoxins Act with a Wide Range of Potencies on SH-SY5Y Human Neuroblastoma Cells. NeuroToxicology 22:447-453, 2001.

Rassetti-Escargueil C., et al, Journal of the International Society on Toxinology. Apr. vol. 53, No. 5, p. 503-511, Apr. 2009.

Second Chinese Office Action from Chinese Application 202080052392.6 dated Aug. 5, 2014.

Sheridan, R.E., et al, Applied Toxicology, vol. 19, Suppl. 1, p. S29-S33, Dec. 1999.

Translation of second Chinese Office Action from Chinese Application 202080052392.6 dated Aug. 5, 2014.

Williamson. L.C., et al., Journal of Biological Chemistry, American Society for Biochemisty and Molecular Biology, vol. 271, No. 13, p. 7694-7699, Mar. 29, 1996.

Wohlfarth, K., et al., Naunyn-Schmiedebergs Archives of Pharmacology, vol. 355, No. 3, p. 335-340, Mar. 1997.

International Preliminary Report on Patentability for PCT/EP2013/074276 dated Jun. 4, 2015.

Jones, R.G.A, et al., "Development of improved SNAP25 endopeptidase immuno-assays for botulinum type A and E toxins", Journal of Immunological Methods 329, 2008, pp. 92-101.

Keller, James E., et al, FEBS Letters 456, 1999, pp. 137-142, "Persistence of botulinum neurotoxin action in cultured spinal cord cells".

McNutt, Patrick, et al, Biochemical and Biophysical Research Communicatioins, 2011, vol. 405, pp. 85-90, Embryonic stem cell-derived neurons are a novel, highly sensitive tissue culture platform for botulinum research.

Vertiev, IuV, et al., "Effective expression of fragments of a botulinum neurotoxin type A gene, coding for the L-chain and H-chain in E. coli, with formation of products causing protective immunity to administration of the toxin", Mol Gen Mikrobiol Virusol. vol. 4, 2000, pp. 3-7.

Malizio, Carl J., et al., Methods in Molecbular Biology, 2000, vol. 145: Bactrial Toxins: methods and Protocols, pp. 27-39, "Purification of Clostridium botulinum type A neurotoxin".

Pellet, Sabine, et al., Biochem Biophys Res Commun. Jan. 7, 2011, vol. 404(I), pp. 388-392, "Sensitive and quantitative detection of botulinum neurotoxin in neurons derived from mouse embryonic stem cells".

Boroff, Daniel., A., et al., Journal of Bacteriology, No. 1966, vol. 92, No. 5, p. 1580-1581, "Statistical analysis of a rapid in vivo method for the titration of the toxin of Clostridium botulinum".

Ekong, Theresa, A., et al., Microbiology, 1997, vol. 143, pp. 3337-3347, "Recombinanat SNAP-25 is an effective substrate for Clostridium botulinum type A toxin endopeptidase activity in vitro".

Ellies, M., Laryngo-Rhino-otol, 2003, vol. 82, pp. 713-714, "Tierexperimentelle und klinische untersuchungen zur sekretionshemmung der kopfspeicheldrüsen durch botulinum toxin A".

Evans, E.R., et al., Journal of Applied Microbiology, 2009, vol. 107, pp. 1384-1391, "An assay for botulinum toxin types A, B and F that requires both functional binding and catalytic activities within the neurotoxin".

Fan, Frank, et al., Assay and Drug Development Technologies, vol. 5, No. 1, 2007, pp. 127-136, "Bioluminescent assays for high-troughput screening".

Fischer, Audrey, et al., PNAS, Jun. 19, 2007, vol. 104, No. 25, pp. 10447-10452, "Single molecule detection of intermediates during botulinum neurotoxin translocation across membranes".

Gossen, Manfred, et al., Proc. Natl. Acad. Sci. USA, Jun. 1992, vol. 89, pp. 5547-5551, "Tight control of gene expression in mammalian cells by tetracycline-responsive promoters".

(56) References Cited

OTHER PUBLICATIONS

Habermann, E., Naunyn-Schmiedeberg's Arch. Pharmacol., 1974, vol. 281, pp. 47-56, "I-labeled neurotoxin from Clostridium botulinum A: preparation, binding to synaptosomes and ascent to the spinal cord".

Hughes, R., et al., J. Physiol. 1962, vol. 160, pp. 221-233, "Influence of nerve-ending activity and of drugs on the rate of paralysis of rat diaphragm preparatioins by CL. botulinum type A toxin".

Jost, Wolfgang, H., et al., Drugs 2007, vol. 65, No. 5, pp. 669-683, "Botulinum neurotoxin type A free of complexing proteins (XEOMIN) in focal dystonia".

Kondo, Hisashi, et al., Japan. J. Med. Sci. Biol., 1984, vol. 37, pp. 131-135, "Titration of botulinum toxins for lethal toxicity by intravenous injection into mice".

Krieglstein, Kerstin, et al., Eur. J. Biochem., 1990, vol. 188, pp. 39-45, "Arrangement of disulfide bridges and positions of sulfhydryl groups in tetanus toxin".

Krieglstein, Kerstin, G., et al., Eur. J. Biochem. 1991, vol. 202, pp. 41-51, "Limited proteolysis of tetanus toxin".

Krieglstein, Kertsin, G., et al., Journal of Protein Chemistry 1994, vol. 13, No. 1, pp. 49-57, "Covalent structure of botulinum neurotoxin type A: location of sulfhydryl groups, and disulfide bridges and identification of C-termini of light and heavy chains".

Lamanna, Carl, et al., Infection and Immunity, Apr. 1970, vol. 1, No. 4, pp. 423-424 "Dependence of time to death on molecular size of botulinum toxin".

Miraglia, Loren, J., et al., Combinatorial Chemistry & High Throughput Screening, 2011, vol. 14, pp. 648-657 "Seeing the light: luminescent reporter gene assays".

Monnier, G., et al., Readapt. Med. Phys. 2003, vol. 46, pp. 338-345 "Hypersialorrhée, hypersudation et toxine botulique sialorrhea, hyperhidrosis and botulinum toxin".

Schiavo, Giampietro, et al., Physiological Reviews, Apr. 2000, vol. 80, No. 2, pp. 717-766 "Neurotoxins affecting neuroexocytosis".

Schokett, Penny, et al., Current Protocols in Molecular Biology 1997, Suppl. 60, pp. 16.14.1-16.14.9 "Inducible gene expression using an autoregulatory, tetracycline-controlled system".

Yu, Junying, et al., Science, May 8, 2009, vol. 324, No. 5928, pp. 797-801, "Human induced pluripotent stem cells free of vector and transgene sequences".

Zhu, Zhou, et al., Cell & Developmental Biology, 2002, vol. 13, pp. 121-128 "Tetracycline-controlled transcriptional regulation systems: advances and application in transgenic animal modeling".

Ellies, M., (English translation) Laryngo-Rhino-Otol, 2003, vol. 82, pp. 713-714, "Tierexperimentelle und klinische untersuchungen zur sekretionshemmung der kopfspeicheldrüsen durch botulinum toxin A".

Monnier, G., et al., (English Translation) Readapt. Med. Phys. 2003, vol. 46, pp. 338-345 "Hypersialorrhée, hypersudation et toxine botulique sialorrhea, hyperhidrosis and botulinum toxin".

\* cited by examiner

COMPOSITIONS AND METHODS FOR TOXIGENICITY TESTING

This application claims priority to U.S. Provisional Application No. 61/540,693, filed Sep. 29, 2011, which is herein incorporated by reference in its entirety.

FIELD OF THE INVENTION

The present invention relates to compositions and methods for testing agents (e.g., *Clostridium botulinum* neurotoxin (BoNT) detection and analysis). In particular, the present invention relates to the use of Human induced pluripotent stem (hiPS) derived cells for agent detection and analysis.

BACKGROUND OF THE INVENTION

Botulinum neurotoxins (BoNTs), synthesized by the Gram-positive, soil-dwelling bacterium *Clostridium botulinum*, are the most toxic substances known to humankind and are the causative agents of the neuroparalytic disease botulism (Johnson E (2005) in *Topley and Wilson's microbiology and microbial infections*, ed S. P. Borriello, P. R. Murray, and G. Funke (Hodder Arnold, London, United Kingdom), pp 1035-1088). Seven immunologically distinct serotypes of BoNTs designated A through G have been described (Gimenez D F & Gimenez J A (1995) *Int J Food Microbiol* 27: 1-9). BoNTs are initially synthesized as a single-chain polypeptide of ~150 kDa, but posttranslational proteolytic cleavage yields distinct heavy and light chains (HC and LC) of ~100 kDa and ~50 kDa linked by a disulfide bond. The HC is further functionally divided into the $HC_C$ and $HC_N$ sub-domains. The $HC_C$ domain is responsible for recognition and binding to specific neuronal cell surface receptors leading to endocytosis, while the $HC_N$ domain is responsible for channel formation in the endocytic vesicle membrane and translocation and internalization of the LC across the endosomal membrane (Montecucco et al., (2004) *Trends Microbiol* 12: 442-446; Fischer A & Montal M (2007) *J Biol Chem* 282: 29604-29611; Fischer A, et al (2009) *Proc Natl Acad Sci USA* 106: 1330-1335). During translocation, the disulfide bond is cleaved, and the LC is released into the cell cytosol and refolded to the active enzyme component as a zinc-dependent endopeptidase (Fischer et al., supra; Fischer A & Montal M (2007) *Proc Natl Acad Sci USA* 104: 10447-10452). The LC then specifically targets and cleaves an intracellular SNARE protein at the pre-synaptic vesicles, which leads to inhibition of neurotransmitter release. Each BoNT serotype has a distinct cleavage target, with BoNT/A and E cleaving SNAP-25 at distinct sites, BoNT/B, D, F, and G cleaving VAMP/synaptobrevin at different sites, and BoNT/C cleaving both SNAP-25 and syntaxin (reviewed in Montecucco C & Schiavo G (1994) *Mol Microbiol* 13: 1-8).

Naturally occurring botulism is a rare but serious disease, with ~110 cases occurring per year in the United States and a lethality rate of ~5-10% (Johnson E A & Montecucco C (2008) in Handbook of Clinical Neurology, ed Andrew G. Engel (Elsevier, pp 333-368). Due to their extreme potency (estimated human lethal dose of 1 ng/kg of body weight for BoNT/A (Bossi P, et al (2006) *Cell Mol Life Sci* 63: 2196-2212), the severity of the disease botulism and the high cost involved in treating cases, especially at a large scale, BoNTs have been classified as a category A Select Agent and present a serious threat as a bioterrorism weapon (Arnon S S, et al (2001) *JAMA* 285: 1059-1070).

BoNT/A and to a much lesser extent BoNT/B are also being used as unique and important pharmaceuticals to treat a variety of neuromuscular disorders and in cosmetics. Conditions for which the Food and Drug Administration approved the use of BoNTs include cosmetic treatments and to temporarily relieve a variety of muscle spasticity disorders, hyperhidrosis and migraines (Chaddock J A & Acharya K R (2011) *FEBS J* 278: 899-904). Cosmetic and clinical applications of BoNTs are increasing, and new formulations of BoNTs for pharmaceutical purposes are being developed necessitating clinical trials, accurate potency determination, and neutralizing antibody screening. For example, BoNTs are pharmaceutically administered for the treatment of pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinossn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor. Thus, the quantitative and reliable detection of BoNT activity in the environment, in foods, in pharmaceutical preparations, for antibody detection, and in research applications is crucial in both prevention of botulism, for counter-terrorism, as well as new drug development and patient safety and quality control and assurance testing of products.

Many BoNT detection methods have been published, and they can be divided into four general categories (reviewed in Cai et al., (2007) *Crit Rev Microbiol* 33: 109-125): 1. in vitro assays that immunologically detect the presence of holotoxin but cannot distinguish between active or inactive states (ELISA); 2. endopeptidase assays that detect the enzymatic activity of the toxin LC but do not distinguish between biologically active holotoxin and the LC only; 3. in vivo assays (mouse bioassay); and lastly 4. in vivo simulation assays such as the hemidiaphragm assay, local injection assays, and cell-based assays using primary or immortalized cells. In order to detect fully active BoNTs, a detection assay should measure all steps of the intoxication process (e.g., HC binding to the cell surface receptors, endocytosis, vesicle channel formation, cleavage of the disulfide bond, transduction of the LC into the cell cytosol, and finally proteolytic cleavage of SNARE proteins). Only the mouse bioassay and the in vivo simulation assays measure all of these steps. The mouse bioassay involves injecting mice either intravenously or intraperitoneally with different dilutions of BoNT, and then observing the mice for symptoms of botulism poisoning (limb paralysis, labored breathing, ruffled fur, etc.) (Hatheway C L (1988) in *Laboratory diagnosis of infectious diseases: principles and practice*. eds Balows A, Hausler W H, Ohashi M & Turano M A (Springer-Verlag, New York), pp 111-133; Schantz EJaK, D. A. (1978) *Journal of the Association of Official Analytical Chemists* 61: 96-99) and ultimately death. Although the MBA is quantitative and can monitor all the steps of intoxication, it has a large error rate, is not standardized between or within labs, requires a large number of animals, and the corresponding facilities and trained staff. The hemidiaphragm and local injection assays reduce the suffering of animals and some are sufficiently sensitive, but still require large numbers of animals and skilled staff.

These clearly identified shortcomings of these assays have incited a recommendation from regulatory agencies including the FDA and USDA to develop a cell-based model that would provide a specific, sensitive, and quantitative alternative to the MBA (National Institute of Environmental Health Sciences, 2008). Various continuous cell lines, including neuro-2a and PC-12, have been used for toxicity testing, but are not sensitive enough to compete with the MBA. Primary neurons derived from rat, mouse, or chicken, and neurons derived from mouse embryonic stem cells are significantly more sensitive (Hall Y H, et al (2004) J Immunol Methods 288: 55-60; Keller J E, Cai F & Neale E A (2004) Biochemistry 43: 526-532; Lalli G, et al (1999) J Cell Sci 112 (Pt 16): 2715-2724; Neale et al., (1999) J Cell Biol 147: 1249-1260; Stahl A M, et al (2007) J Biomol Screen 12: 370-377). The most sensitive cell type for toxicity testing and antibody detection described is the primary rat spinal cord cells (RSC) assay (Pellett et al., (2007) *FEBS Lett* 581: 4803-4808), which is more sensitive than the MBA, reproducible, and correlates well with the mouse bioassay (Pellett et al., (2010) *J Pharmacol Toxicol Methods*). Additionally, neurons derived from embryonic stem cells have also been shown to be highly sensitive (McNutt et al., (2011) *Biochem Biophys Res Commun* 405: 85-90; Pellett S, et al (2011) *Biochem Biophys Res Commun* 404: 388-392; Kiris E, et al (2011) *Stem Cell Res*). However, the RSC assay still requires the use of some animals and skilled staff for cell preparation, and is not easily adaptable to testing standardization due to the need to continuously prepare new batches of cells.

SUMMARY OF THE INVENTION

The present invention relates to compositions and methods for testing agents (e.g., *Clostridium botulinum* neurotoxin (BoNT) detection and analysis). In particular, the present invention relates to the use of Human induced pluripotent stem (hiPS) derived cells for agent detection and analysis.

Embodiments of the present invention provide neuronal cells (e.g., human (e.g., iPS derived)) for use in research, screening, clinical and therapeutic applications. In some embodiments, the methods are used in the detection and analysis of BoNT and neutralizing antibodies to BoNT. Exemplary embodiments are described herein and below. Additional embodiments are described herein and are within the knowledge of one of skill in the art.

For example, in some embodiments, the present invention provides a method of assaying a clostrial species (e.g., *Clostridium botulinum* neurotoxin (BoNT)) for activity, comprising: a) contacting a human induced pluripotent stem cell (hiPS) derived neuronal cell with a composition comprising a NT; and b) assaying the NT for biological activity. In some embodiments, the clostrial species is *Clostridium botulinum*, *Clostridium butyricum*, or *Clostridium baratii*. In some embodiments, the BoNT encompasses all seven known serotypes including serotypes A, B, C, D, E, F, and G and known subtypes within each serotype. In some embodiments, the NT is a recombinant, mutant or chimeric NT. In some embodiments, the biological activity is cleavage of SNAP-25, VAMP or syntaxin. In some embodiments, the assay is qualitative, while in others it is quantitative. In some embodiments, the NT is purified, while in others it is in a complex, a solution or a matrix. In some embodiments, the NT is recombinant. In some embodiments, the NT is conjugated with another molecule selected from therapeutic modalities, markers, imaging agents, enzymes, receptors, antibodies, or bioactive compounds. In some embodiments, the method further comprises the step of contacting the NT with a test compound prior to contacting the hPS derived neuronal cells. In some embodiments, the test compound is an antibody (e.g., a neutralizing antibody) or small molecular inhibitor of NT. In some embodiments, the neutralizing antibody is purified or in a serum or antitoxin sample.

The present invention further provides a method of assaying a clostrial species neurotoxin (e.g., BoNT) for activity, comprising: a) contacting a human induced pluripotent stem (hiPS) derived neuronal cell with a composition comprising a) a NT; and b) a neutralizing antibody; and b) assaying the NT for biological activity.

The present invention also relates to a method for determining the amount of biologically active BoNT in a preparation comprising biologically active BoNT and, preferably, a pharmaceutical preparation comprising biologically active BoNT. In some embodiments, the method comprises the steps of: (a) contacting a hiPS cell derived neuronal cell with a sample of a preparation comprising biologically active BoNT; and (b) determining the amount of biologically active BoNT present in the preparation by assaying the sample for the biological activity of BoNT.

In further embodiments, the present invention provides the use of a human induced pluripotent stem (hiPS) cell derived neuronal cell for assaying a BoNT for activity.

Additional embodiments are described herein.

DESCRIPTION OF THE FIGURES

Figure 8:
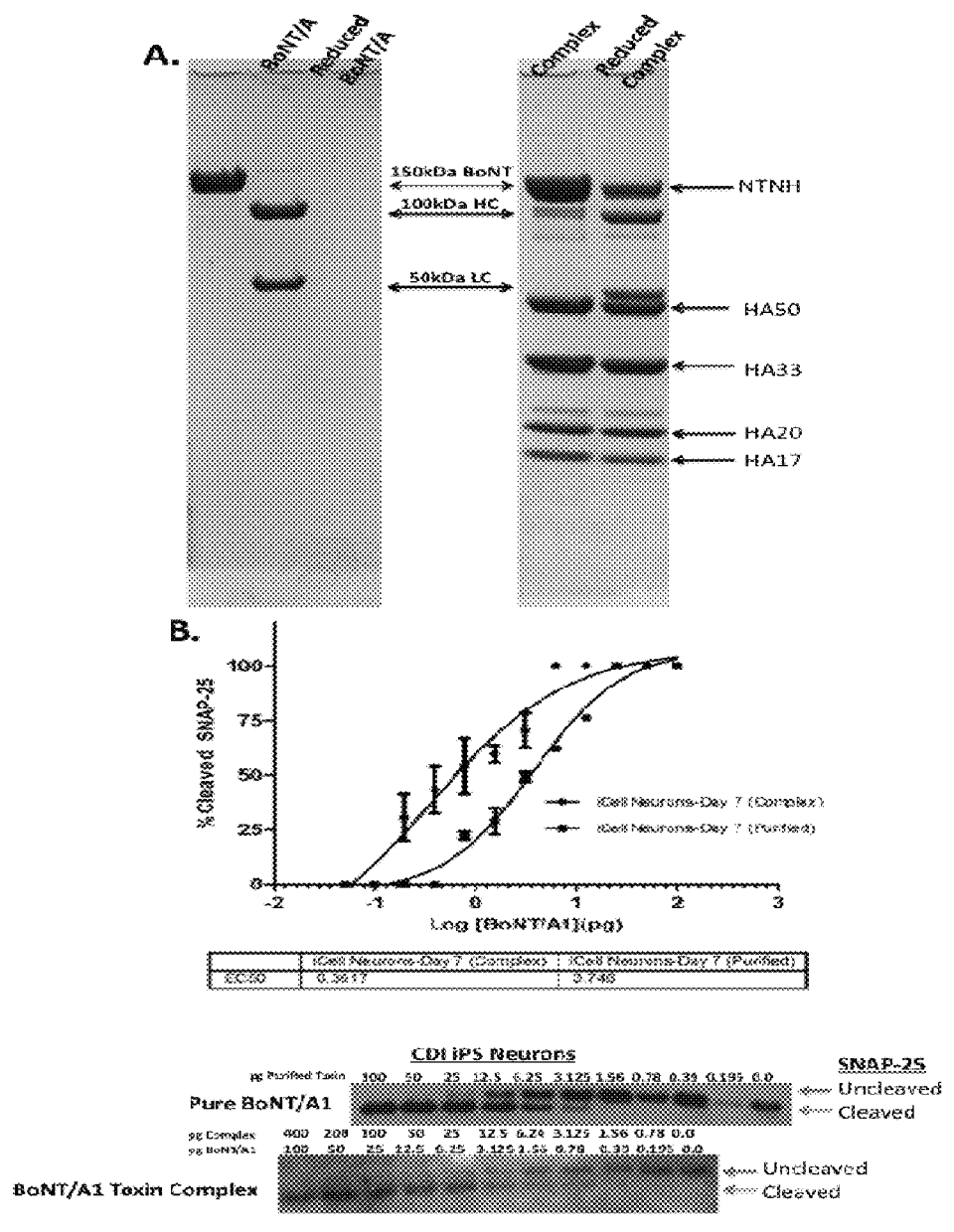

FIG. 8 shows sensitivity of iPS neurons to BoNT/A complex and purified BoNT/A A. SDS-PAGE gel comparing purified BoNT/A1 and BoNT/A1 complex (ladder from Invitrogen: SeeBlue® Plus2 Pre-Stained Standard). B. Sensitivity of iPS neurons to BoNT/A1 purified toxin and BoNT/A1 complex after 48 h toxin exposure.

Figure 9:
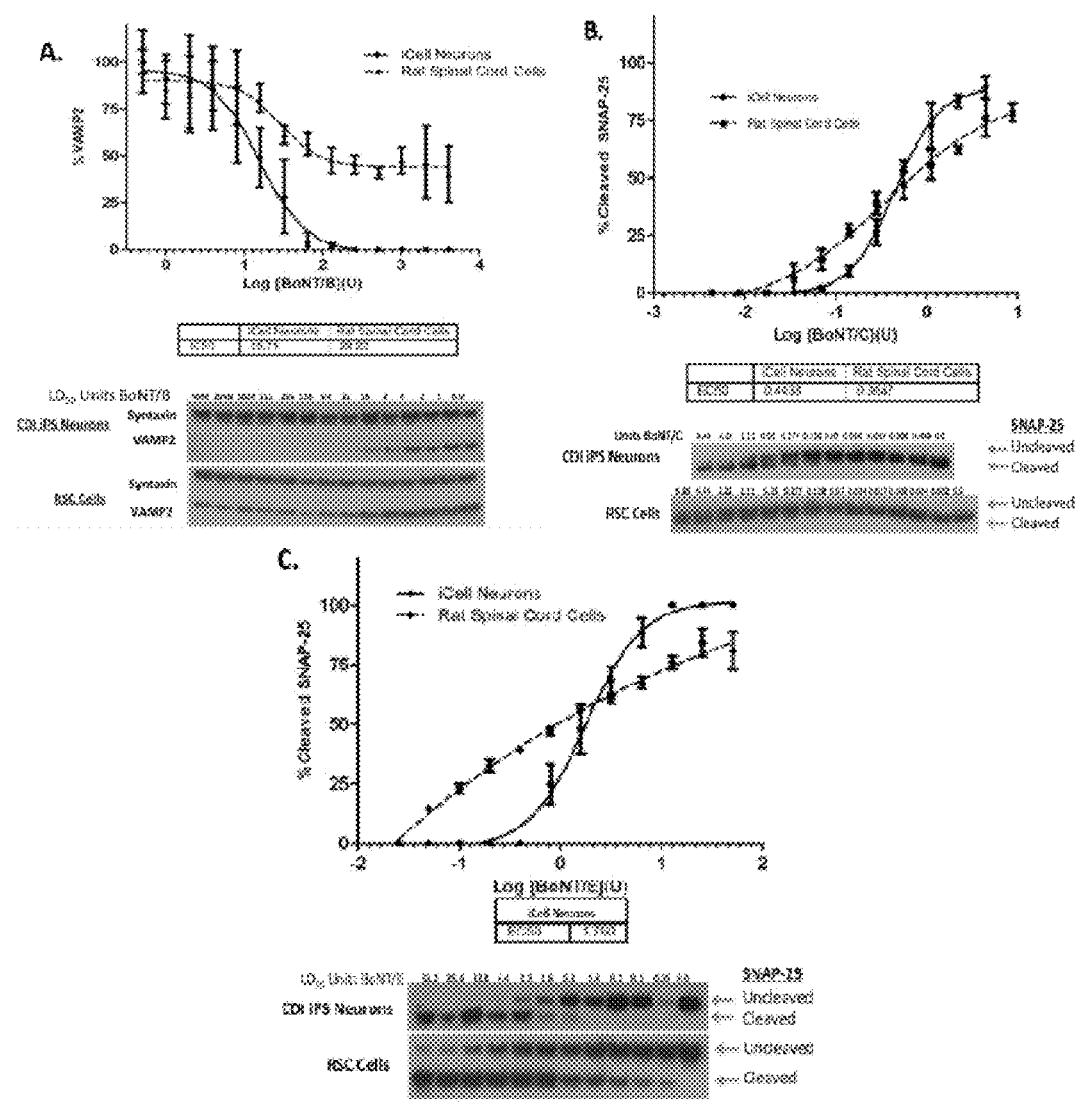

FIG. 9 shows detection of BoNT/B, C, and E activity in iPS neurons. The iPS neurons matured for 7 days and RSC cells were exposed to serial dilutions of BoNT/B (A), /C (B), and /E (C) for 48 h in parallel.

DEFINITIONS

Figure 1:
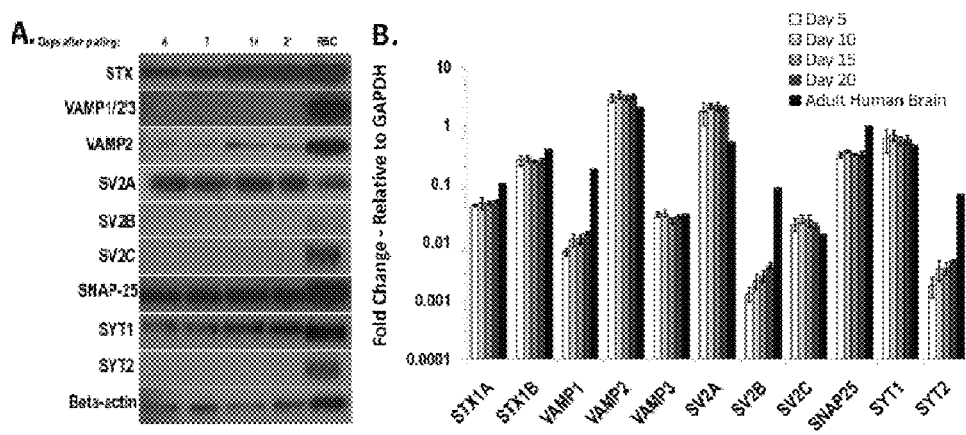
FIG. 1 shows BoNT receptor expression in iPS neurons A. iPS cells were matured for 4, 7, 10, 14 and 21 days and assayed via Western blot for expression levels of BoNT receptors. B. iPS cells were matured for 5, 10, 15 and 20 days and adult human brain cells were used to perform quantitative-PCR assays.

To facilitate an understanding of the present invention, a number of terms and phrases are defined below:

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vitro, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the terms "detect", "detecting" or "detection" may describe either the general act of discovering or discerning or the specific observation of a detectably labeled composition.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include cells, tissues, blood products, such as plasma, serum and the like. Such examples are not however to be construed as limiting the sample types applicable to the present invention. In some embodiments, the sample can also be a sample of a preparation comprising biologically active BoNT, such as a BoNT preparation to be applied for pharmaceutical or cosmetic purposes. Moreover, in an aspect of the disclosure, the sample may also be an environmental sample or a food sample suspected to comprise BoNTs.

DETAILED DESCRIPTION OF THE INVENTION

The present invention relates to compositions and methods for testing agents (e.g., Clostridium botulinum neurotoxin (BoNT) detection and analysis). In particular, the present invention relates to the use of Human induced pluripotent stem (hiPS) derived cells for agent detection and analysis.

Embodiments of the present invention provide systems and methods for the detection and analysis of BoNT. In some embodiments, the systems and assays utilize human iPS derived neurons as a highly sensitive and reproducible platform for botulinum neurotoxin (BoNT) detection. In some embodiments, the neurons are a 98% pure pan-neuronal population of GABAergic, dopaminergic, and glutamatergic neurons and are produced and cryopreserved as differentiated cells. In another aspect, the neurons are an essentially pure pan-neuronal population of GABAergic, dopaminergic, and glutamatergic neurons and are produced and cryopreserved as differentiated cells, wherein the cells are at least 70%, at least 80%, at least 90%, at least 95% or at least 96% pure with respect to the neuronal cells. Experiments conducted during the course of development of embodiments of the present invention demonstrated that the cells express all the necessary receptors and substrates for BoNT intoxication by all BoNT serotypes. BoNT detection assays demonstrate that the iPS-derived neurons are highly sensitive for quantitative detection of BoNT/A, B, C, and E and neutralizing antibodies.

In November of 2007, two independent groups showed for the first time that human fibroblast cells can be reprogrammed to pluripotent stem cells simply by activating a small set of silenced genes (Takahashi K, et al (2007) *Cell* 131: 861-872; Yu J, et al (2007) *Science* 318: 1917-1920). These cells were termed induced pluripotent stem cells and can be maintained and cryopreserved similar to cell lines. This discovery opens the opportunity for the development of a vast number of human iPS derived cell models that resemble fully functioning, differentiated human somatic cells and do not require any animal use.

In selecting iPS cells for use in the systems and methods described herein, it is preferred that the cells can be reliably and reproducibly produced and generate pure populations of differentiated cells in sufficient quantities for such studies. In some embodiments, such cells are available from Cellular Dynamics Inc. (Madison, Wis.).

Experiments conducted during the course of development of embodiments of the present invention demonstrated that human iPS-derived neurons are a highly sensitive, selective, and species-specific cell model for the detection of the botulinum neurotoxins, neutralizing antibodies and inhibitors, and for BoNT cell entry and trafficking studies. These neurons are suitable to replace the MBA for BoNT potency determination as well as for antibody detection, screening of inhibitors, and research applications.

I. Cells

As described herein, embodiments of the present invention provide pluripotent derived stem cells for use in the detection and analysis of agents such as BoNT. In some embodiments, the cells are human (e.g., human induced pluripotent stem derived cells (hiPS) derived neuronal cells or human embryonic stem cells). Methods of generating iPS cells are described, for example, in Yu et al., Science. 2009 May 8; 324(5928):797-801. Epub 2009, WO2011056971 and WO2011025852, each of which is herein incorporated by reference in its entirety. In some embodiments, iPS cells are differentiated into neurons using suitable methods (e.g., those described in U.S. Patent Applications US2010/0279403 and US2010/0216181, each of which is herein incorporated by reference in its entirety).

In some embodiments, the neurons are a 98% pure pan-neuronal population of GABAergic, dopaminergic, and glutamatergic neurons and are produced and cryopreserved as differentiated cells. In some embodiments, commercially available neuronally derived iPS cells (e.g., those available from Cellular Dynamics Inc. (Madison, Wis.) or GlobalStem, (Rockville, Md.)) are utilized, although other sources may be utilized. In some embodiments, cells are neuronal hiPS cells.

In another aspect, the cells are the neurons are an essentially pure pan-neuronal population of GABAergic, dopaminergic, and glutamatergic neurons and are produced and cryopreserved as differentiated cells, wherein the cells are at least 70%, at least 80%, at least 90%, at least 95% or at least 96% pure with respect to the neuronal cells.

The present invention is not limited to the cells described herein. Additional cell lines and primary cell cultures may be utilized. For example, in some embodiments, cholinergic neurons are utilized.

In some embodiments, suitable cell lines express receptors and substrates necessary or sufficient for BoNT intoxication.

In some embodiments, the present invention provide systems and kits comprising the cell lines described herein, along with components necessary, sufficient or useful for performing detection and analysis of BoNT. For example, in some embodiments, the kits comprise cells and cell culture reagents (e.g., plates, buffers, etc.), assay reagents, controls (positive and negative BoNT and/or inhibitor controls) and instructions for performing and analyzing assays.

In an aspect of the invention, the hiPS cell derived neuronal cell is obtainable or has been obtained by differentiation and/or maturation of a hiPS cell generated by a process as referred to above into a neuronal cell. Such neuronal cell differentiation, in an aspect, can be achieved by cultivation of the hiPS cells at about 37° C. and under about 5% $CO_2$. In an aspect, the medium for cultivation may be Neurobasal medium supplemented with B27 and glutamax (Invitrogen, Inc., USA). In yet another aspect, cells are cultivated on poly-lysine coated plates and, in yet a further aspect, plates are in addition coated with matrigel (BD Bioscience, USA). In an aspect, a 96 well plate is used for cultivation wherein the cells are grown at a density of about 40,000 cells per well. In an aspect, cells are allowed to seed for about 24 hours. Afterwards, the cells are allowed in an aspect to mature for about 2 to about 28 days, in an aspect, about 4 to about 14 or, in an aspect, about 4 to about 7 days.

In an aspect, the said hiPS cell derived neuronal cells are obtained by a differentiation and maturation process essentially as described in the accompanying Examples, below.

Embodiments of the present invention also relate to a hiPS cell derived neuronal cell obtained by the aforementioned differentiation and maturation process.

In an aspect, such a hiPS cell derived neuronal cell is characterized by the presence of one or more and, in an aspect all, of the following markers: β3-tubuline, NeuN, vGAT, vGLUT2, NSE neurone-specific enolase) or Tbr1 (T-domain transcription factor 1). For β3-tubuline or NeuN it is envisaged that the number of positive cells in a culture of the hiPScell derived neuronal cell of the invention is about 99%. For vGAT or vGLUT2 it is envisaged in an aspect that at least a portion of the cells of the culture are positive for the said markers.

In an aspect, such a hiPS cell derived neuronal cell is characterized by the absence of one or more and, in an aspect all, of the following markers: GFAP, TH, NNE (non-neuronal enolase), Tbr2 (T-domain transcription factor 2), or NoGo a, C. For GFAP it is envisaged that the number of positive cells in a culture of the hiPS cell derived neuronal cell is significantly low and, in an aspect, below about 5% or even below about 1%, for the remaining markers it is in an aspect envisaged that they are, if at all, present below a detectable amount.

The presence or absence or the amount of the aforementioned markers may, in an aspect, be determined by conventional immunological techniques. For example, the markers can be determined by immunohistological staining techniques, Western blot analysis of cell lysates or, as far as β3-tubuline or NeuN are concerned by FACS analysis. Further detection techniques are described (see, e.g., US2012/0178083, US2008/0280301, Englund 2005, J Neurosci 25: 247-251; Dupuis 2002, Neurobiology of Diseases 10: 358-365; each of which is herein incorporated by reference).

In a further aspect, the hiPS cell derived neuronal cell is characterized by at least one and, in an aspect all, of the following electrophysiological properties: inhibition of Na2+ channels by tertrodotoxin (TTX), inhibition of K+ channels by tetraethylammonium, inhibition of L-type Ca2+ channels by nifedipin, inhibition of P/Q-type Ca2+ channels by w-aga-toxin IVA or inhibition of N-type Ca2+ channels by w-cono-toxin GVIA. Such electrophysiological properties can be tested by standard electrophysiological measurements including, e.g., patch-clamp measurements before and after treatment of the cells with the respective inhibitors.

In another aspect, the hiPS cell derived neuronal cell is characterized by sensitivity to BoNT and, in an aspect, BoNT/A. Moreover, the cells, in an aspect, are also sensitive to other neurotoxic compounds in a dose dependent manner and, in particular, to at least one or all of the following compounds: staurosporine, ATP competitive kinase inhibitor, chloropromazoine or phenothiazine. The sensitivity towards the aforementioned compounds can be determined in, e.g., cell viability assays.

In an aspect the hiPS cell derived neuronal cells are also sensitive with respect to neurite outgrowth to at least one and, in an aspect all, of the following compounds: antimycin A, mitomycin C, MK571, PD98092 or staurosporine.

Further, in an aspect the hiPS cell derived neuronal cells are sensitive with respect to mitochondrial membrane potential loss to at least one or, in an aspect, all of the following compounds: antimycine A or valinomycine.

II. Assays and Uses

Embodiments of the present invention provide compositions and methods for assaying BoNT. The assays find use in research, clinical, diagnostic, and therapeutic applications.

In some embodiments, the assays utilize pluripotent cells (e.g., hiPS derived neuronal cells). The use of human cells provides the advantage of a species-specific model. In addition, neurons derived from pluripotent cells are representative of normal, healthy neurons as opposed to neurons derived from cancer cell lines or modified cell lines, which may not be reflective of somatic neurons.

In some embodiments, assays utilize neuronal cells e.g., hiPS derived neuronal cells to screen the potency of BoNT. In other embodiments, assays screen for toxicity of BoNT. In still further embodiments, assays screen for the presence of or properties of neutralizing antibodies for BoNT or other biopharmaceuticals for activity. In some embodiments, assays are quantitative, while in others they are qualitative.

In some embodiments, cells are first cultured on a suitable matrix. In some embodiments, cells are cultured in order to obtain maturation of neurons. The pluripotent cells used in embodiments of the present invention provide the advantage of more rapid maturation than cells used in existing assays. In some embodiments, cells are next exposed to toxin (e.g., BoNT) for a suitable time period. Following toxin exposure, desired parameters (e.g, EC50) are calculated using suitable methods. The assays described herein are suitable for detection of both purified BoNT and BoNT in complexes (e.g., complexed with other proteins as found in native settings and some pharmaceutical preparations). The assays described herein are suitable for detection of any number of BoNT serotypes (e.g., BoNT/A, B, C, D, E, F and G) or variants or chimeras thereof. In some embodiments, BoNTs are recombinantly expressed. In other embodiments, they are purified from bacterial cells.

In some embodiments, antibody protection assays are performed to test neutralizing antibodies. Although BoNTs are used effectively in treating a large number of patients for various conditions (reviewed in Dhaked et al., *Indian J Med Res* 132: 489-503), some will develop neutralizing antibodies, which will prevent the success of further treatments. For example, it is estimated in the treatment of cervical dystonias that ~5% of the treated patients will develop neutralizing BoNT antibodies that will impede further treatment (Kessler et al., (1999) J Neurol 246: 265-274). Currently, patients are not monitored over the course of their treatments for development of neutralizing antibodies because a highly sensitive and quantitative assay is not commercially available (Sesardic et al., (2004) *Mov Disord* 19 Suppl 8: S85-91). The testing platform presented here using iPS neurons provides sensitive and quantitative detection of BoNT-neutralizing antibodies in the sera of patients who have received repeated therapeutic or cosmetic injections of BoNT. Neutralizing antibodies can be detected in any number of sample types (e.g., purified antibodies, serum, antitoxins, etc.).

In some embodiments, small molecule inhibitors of BoNTs are tested (e.g., for research or drug screening). For example, in some embodiments, cells are exposed to either the BoNT first, then the inhibitor, co-exposed to both, or the cells are exposed to the inhibitor first, then BoNT.

Any number of suitable endpoint measurements may be utilized to assay BoNT activity. Examples include, but are not limited to, Western blot, neurotransmitter release, ELISA (Nuss J E, et al (2010) *J Biomol Screen* 15: 42-51) or intracellularly expressed reporters such as, for example, FRET sensors (Dong et al., (2004) *Proc Natl Acad Sci USA* 101: 14701-14706).

In some embodiments, the assays described herein find use in testing of quality controls during production of BoNTs or derivatives as pharmaceuticals or for research use, in diagnostic assessment, in the optimization and dosing of clinical treatment and in the selection of therapeutic modality.

Additional applications of the assays described herein include, but are not limited to, detection of inhibitors and diagnostic, clinical, screening and research uses.

In some embodiments, the present invention provides a method for assaying a *Clostridium botulinum* neurotoxin (BoNT) for activity, comprising: a) contacting a hiPS derived neuronal cell with a composition comprising a BoNT; and b) assaying the BoNT for biological activity.

In an aspect of the said method, the assaying may comprise determining the presence or absence of biological activity of BoNT. Such an assay may be sometimes also referred to herein as qualitative assay. It will be understood that based on the presence or absence of BoNT biological activity, it may be concluded on the presence or absence of biologically active BoNT in a composition comprising or suspect to comprise said biologically active BoNT. Moreover, in yet another aspect, assaying may encompass determining the amount of biologically active BoNT in a composition comprising biologically active BoNT. It will be understood that the amount of biologically active BoNT can be derived from the amount of biological activity assayed for the said BoNT in the composition. Such an assay may be sometimes also referred to as quantitative assay herein.

In an aspect of the method of the present invention, the BoNT is a neurotoxin selected from the different serotype groups for clostridial neurotoxins, e.g., is selected from, for example, BoNT/A, BoNT/B, BoNT/C1, BoNT/D, BoNT/E, BoNT/F, or BoNT/G. Moreover, in an aspect, Tetanus toxin (TeNT) may be used as a neurotoxin in the methods according to the present invention.

The bacteria *Clostridium botulinum* and *Clostridium tetani* naturally produce these highly potent neurotoxins, e.g., botulinum toxins (BoNTs) and tetanus toxin (TeNT), respectively. These neurotoxins specifically bind to neuronal cells and disrupt neurotransmitter release. Each toxin is synthesized as an inactive single-chain protein of approximately 150 kDa. The posttranslational processing involves formation of disulfide bridges, and limited proteolysis (nicking) by bacterial protease(s). Active dichain neurotoxin consists of two chains, an N-terminal light chain of approx. 50 kDa and a heavy chain of approx. 100 kDa linked by a disulfide bond. Neurotoxins structurally consist of three domains, e.g., the catalytic light chain, the heavy chain encompassing the translocation domain (N-terminal half) and the receptor binding domain (C-terminal half), see, e.g., Krieglstein 1990, Eur J Biochem 188, 39; Krieglstein 1991, Eur J Biochem 202, 41; Krieglstein 1994, J Protein Chem 13, 49. The structures of the BoNT polypeptides and TeNT polypeptide have been described in the aforementioned references.

The seven antigenically distinct serotypes of BoNTs and TeNT are $Zn^{2+}$-endoproteases that block synaptic exocytosis by cleaving SNARE proteins. Neurotoxins cause the flaccid muscular paralysis seen in the botulism and tetanus disorders, see Fischer 2007, Proc Natl. Acad. Sci. USA 104, 10447.

In yet another aspect, the activity of a modified BoNT or TeNT may be assayed in the method of the invention. Such a modified BoNT can be derived from the aforementioned BoNT/A, BoNT/B, BoNT/C1, BoNT/D, BoNT/E, BoNT/F, or BoNT/G or from TeNT by introducing at least one substitution, addition and/or deletion into the amino acid sequence of the BoNT or TeNT. Such a modified BoNT or TeNT, thus, can have an amino acid sequence being at least 40%, at least 50%, at least 60%, at least 70%, at least 75%, at least 80%, at least 85%, at least 90%, at least 95%, at least 98% or at least 99% identical to the amino acid sequence of any one of the BoNTs or TeNT referred to above. The term "identical" as used herein refers to sequence identity characterized by determining the number of identical amino acids between two amino acid sequences wherein the sequences are aligned so that the highest order match is obtained. It can be calculated using published techniques or methods codified in computer programs such as, for example, BLASTP or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

In an aspect, each of the aforementioned modified BoNT or TeNT polypeptides retain one or more and, in another aspect, all of the biological properties of the respective unmodified polypeptide, i.e. the BoNT/A, BoNT/B, BoNT/C1, BoNT/D, BoNT/E, BoNT/F, BoNT/G or TeNT. Those of skill in the art will appreciate that full biological activity is maintained after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by, e.g., Dressler et al. (Dressler 2005, Mov Disord 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the modified polypeptides may have improved or altered biological properties, e.g., they may comprise cleavage sites which are improved for enzyme recognition or may be improved for receptor binding or any other property specified above.

In an aspect, the modified BoNTs or TeNT may be assayed for one or more and, in an aspect, all of the biological activities referred to above by the method described herein.

In an aspect of the invention, a modified BoNT or TeNT is selected from, for example, BoNT or BoNt/TeNT hybrids, retargeted BoNTs, retargeted TeNT, and chimeric BoNTs or TeNT. Modified BoNTs and TeNT are described.

In an aspect of the method of the invention, contacting comprises bringing at least two different components in physical proximity as to allow physical and/or chemical interaction of said components. In the aforementioned method, the hiPS derived neuronal cell is brought into contact with a composition comprising or suspected to comprise biologically active BoNT. Contacting is carried out for a time and under conditions sufficient to allow for the biologically active BoNT comprised in the composition to exert it's biologically activity on the hiPS cell derived neuronal cell. In an aspect, thus, the contacting shall allow for (a) receptor binding, (b) internalization, (c) translocation across the endosomal membrane into the cytosol, and/or (d) endoproteolytic cleavage of proteins involved in synaptic vesicle membrane fusion or substrates mimicking said process in the hiPS cell derived neuronal cell. The person skilled in the art is well aware of which conditions need to be applied for a given culture of hiPS cell derived neuronal cells. Contacting may, in an aspect, be carried out in a cell culture system wherein the hiPS cell derived neuronal cells are cultured on well plates in a suitable culture medium and under suitable culture conditions by adding to the culture medium a sample of the composition to be assayed for BoNT activity by the methods described herein.

In an aspect, suitable culture conditions comprise cultivation at about 37° C. and under about 5% $CO_2$. In an aspect, the medium for cultivation is Neurobasal medium supplemented with B27 and glutamax (Invitrogen, Inc., USA). In yet another aspect, the hiPS cell derived neuronal cells are cultivated on poly-lysine coated plates and, in yet a further aspect, plates which are in addition coated with matrigel (BD Bioscience, USA) are utilized. In an aspect, a 96 well plate is used for cultivation wherein the cells are grown at a density of about 10,000 to about 100,000 cells, in a further aspect about 20,000 to about 60,000 cells and yet in an aspect about 40,000 cells per well. In an aspect, cells are allowed to seed for about 24 hours. In an aspect, afterwards, the cells are allowed to mature for about 2 to about 28 days, in an aspect, about 4 to about 14 or, in an aspect, about 4 to about 7 days before the contacting is carried out.

In yet an aspect, the said contacting is carried out as described in the accompanying Examples, below.

In an aspect of the method of the present invention, the composition comprising biologically active BoNT is a composition known to comprise biologically active BoNT or a composition suspected of comprising biologically active BoNT. The composition may comprise other ingredients in addition to the said biologically active BoNT such as, for example, a suitable solvent and/or stabilizing agents such as proteins and, in aspect, the complexing proteins of the BoNTs (HA70, HA17, HA33, or NTNH (NBP)), or other protein stabilizers. The composition may also further comprise proteins that facilitate the biological activity of the BoNT, e.g., by enhancing any of the biological activities of the BoNTs referred to elsewhere herein. In yet an aspect, the composition may comprise more than one BoNT.

In an aspect, the composition is a cell lysate of Botulinum or other bacterial cells or non-bacterial cells comprising the biologically active BoNT. In an aspect, such a composition is also a BoNT preparation obtained from such a cell lysate by partial purification, e.g. a crude extract, or purification of the BoNT, e.g., a purified BoNT preparation. In another aspect, the composition is an artificial composition comprising admixed components. In yet an aspect, the composition is a preparation to be used as pharmaceutical composition as defined elsewhere herein.

In an aspect of the method of the present invention, assaying the BoNT for biological activity is carried out by determining the endoproteolytic cleavage of proteins involved in synaptic vesicle membrane fusion or other substrates being cleaved by the biologically active BoNT, if present, in the hiPS cell derived neuronal cell.

In some embodiments, the proteins involved in synaptic vesicle membrane fusion or other substrates have a neurotoxin cleavage site recognized by the BoNT or TeNT to be assayed. A neurotoxin cleavage site as used herein refers to cleavage site which is recognized and cleaved by the endogenous protease of a neurotoxin polypeptide. Cleavage sites which are recognized by the neurotoxin proteases are described (see, e.g., EP 1 926 744 B1; herein incorporated by reference in its entirety). In principle, a neurotoxin cleavage site can be a cleavage site which naturally occurs in a substrate or which is an artificially designed cleavage site recognized and cleaved by the neurotoxin polypeptides protease.

A neurotoxin cleavage site recognized and cleaved by the BoNT/A protease, in an aspect of the invention, is derived from a protein that is sensitive to cleavage by BoNT/A. In an aspect, such a protein is human SNAP25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed in EP 1 926 744 B1.

A neurotoxin cleavage site recognized and cleaved by the BoNT/B protease, in an aspect of the invention, is derived from a protein that is sensitive to cleavage by BoNT/B. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed, for example, in EP 1 926 744 B1.

A neurotoxin cleavage site recognized and cleaved by the BoNT/C1 protease, in an aspect of the invention, is derived from a protein that is sensitive to cleavage by BoNT/C1. In an aspect, such a protein is human and mouse Syntaxin 1A, Syntaxin 1B1, Syntaxin 2-1, Syntaxin 2-2, Syntaxin 2-3, Syntaxin 3A or Syntaxin 1B2, bovine or rat Syntaxin 1A, Syntaxin 1B1 or Syntaxin 1B2, rat Syntaxin 2 or Rat syntaxin 3, mouse Syntaxin 1A, Syntaxin 1B1, Syntaxin 1B2, Syntaxin 2, Syntaxin 3A, Syntaxin 3B or Syntaxin 3C, chicken Syntaxin 1A or Syntaxin 2; *Xenopus* Syntaxin 1A or Syntaxin 1B, *Danio* Syntaxin 1A, Syntaxin 1B or Syntaxin 3, *Torpedo* Syntaxin 1A or Syntaxin 1B, *Strongylocentrotus* Syntaxin 1A or Syntaxin 1B, *Drosophila* Syntaxin 1A or Syntaxin 1B, *Hirudo* Syntaxin 1A or Syntaxin 1B, *Loligo* Syntaxin 1A or Syntaxin 1B, *Lymnaea* Syntaxin 1A or Syntaxin 1B or any ortholog, paralog or homolog thereof. Suitable cleavage sites derived from the proteins are disclosed, for example, in EP 1 926 744 B1.

A neurotoxin cleavage site recognized and cleaved by the BoNT/D protease, in an aspect of the invention, is derived from a protein that is sensitive to cleavage by BoNT/D. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from the proteins are disclosed, for example, in EP 1 926 744 B1.

A neurotoxin cleavage site recognized and cleaved by the BoNT/E protease, in an aspect of the invention, is derived from a protein that is sensitive to cleavage by BoNT/E. In an aspect, such a protein is, such a protein is human SNAP-25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from the proteins are disclosed, for example, in EP 1 926 744 B1.

A neurotoxin cleavage site recognized and cleaved by the BoNT/F protease, in an aspect of the invention, is derived from a protein that is sensitive to cleavage by BoNT/F. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from the proteins are disclosed, for example, in EP 1 926 744 B1.

A neurotoxin cleavage site recognized and cleaved by the BoNT/G protease, in an aspect of the invention, is derived from a protein that is sensitive to cleavage by BoNT/G. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from the proteins are disclosed, for example, in EP 1 926 744 B1.

A neurotoxin cleavage site recognized and cleaved by the TeNT protease, in an aspect of the invention, is derived from a protein that is sensitive to cleavage by TeNT. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from the proteins are disclosed, for example, in EP 1 926 744 B1.

A neurotoxin cleavage site recognized and cleaved by the BoNT proteases, in another aspect of the invention, is derived from the autocatalytic cleavage sites found in the BoNT proteins. In aspects, a neurotoxin cleavage site to be used in accordance with the present invention and which is derived from the autocatalytic cleavage site of a given BoNT or TeNT comprises at least 6, at least 8, at least 10 or at least 15 consecutive residues of including the BoNT/A residues 250Tyr-251Tyr, the BoNT/B residues 256Phe-257Phe, the BoNT/C1 residues 257Phe-258Tyr, the BoNT/D residues 257Phe-258Phe, the BoNT/E residues 239Pro-240Leu, the BoNT/F residues 254Pro-255Leu, the BoNT/G residues 256Phe-257Phe, the TeNT residues 259Ile-260Tyr, the BoNT/A residues Phe266-Gly267, the BoNT/B residues Phe272-Gly273, the BoNT/C1 residues Phe273-Gly274, the BoNT/D residues Phe273-Gly274, the BoNT/E residues Phe255-Gly256, the BoNT/F residues Phe270-Gly271, the BoNT/G residues Phe272-Gly273 or the TeNT residues Phe275-Gly276. Suitable cleavage sites derived from the proteins are disclosed, for example, in EP 1 926 744 B1.

In an aspect of the present invention, cleavage of the aforementioned neurotoxin cleavage sites for BoNTs and TeNT can be assayed by determining one or more cleavage products obtained by the cleavage of the aforementioned proteins. Products derived from the proteins may be determined by antibodies which specifically bind to the said cleaved products but not to the uncleaved proteins. The binding of such specifically binding antibodies to the products may be determined by techniques described herein or elsewhere. For example, the specifically binding antibodies may be covalently or non-covalently linked to a detectable label. Such a detectable label may be a detectable moiety covalently linked to the specifically binding antibody or it may be a detection agent, such as a detection antibody or aptamere which specifically binds to the specifically binding antibody and allows for detection, e.g., via a detectable moiety covalently linked thereto. Various types of such immunoassays can be used in this manner for determining the cleaved products and, thus, for assaying the biological activity of a BoNT or TeNT.

In one aspect, the cleavage of proteins having a neurotoxin cleavage site as defined herein can be determined by Western Blot. In another aspect, said cleavage can be determined by ELISA, RIA or other immunological assay formats including those mentioned elsewhere herein.

In another aspect, an artificial substrate may be used which comprises a neurotoxin cleavage site as specified above and which upon cleavage at said site is altered in at least one physical and/or chemical property. For example, substrates envisaged in such an aspect may comprise a first and a second moiety capable of interacting physically and/or chemically with each other and being separated by a linker having the neurotoxin cleavage site. As a result of the cleavage of the cleavage site, the aforementioned interaction between the two moieties will be altered. Suitable moieties are, e.g., donor and acceptor fluorophores which exhibit resonance energy transfer in the uncleaved state, said resonance energy transfer being interrupted after cleavage. Alternatively, a fluorophore and a quencher may be applied wherein the quenching effect of the quencher is reversed after cleavage. Substrates of said kind are described, e.g., in any one of EP 1 438 586 B1, EP 2 208 067 A1, EP 1 543 329 A2, EP 1 869 459 B1, EP 2 293 064 B1, EP 1 920 248 B1, EP 2 264 458 A1, EP 2 332 959 A2, WO 2011/47241, EP 1 901 069 B1, EP 2 293 064 B1, EP 1 807 698 B1 or EP 2 107 112 B1; each of which is herein incorporated by reference in its entirety.

In yet one specific aspect of the method of the invention, the assaying is carried out by determining the amount of cleaved SNAP-25 present in the hiPS cell derived neuronal cell by determining the amount of cleaved SNAP-25 using a first antibody and, in an aspect, a monoclonal antibody which specifically binds to said cleaved SNAP-25. Moreover, the total SNAP-25 present in the cells, e.g., cleaved and uncleaved SNAP-25, is determined by a second antibody and, in an aspect, a polyclonal antibody binding to said total SNAP-25. In an aspect, the amount of bound first antibody and the amount of bound second antibody can be determined by a detection agent, in an aspect, by one or more detection antibodies allowing to distinguish between the amount of bound first and the amount of bound second antibodies. For example, a first detection antibody coupled to a first label and binding to the first antibody and a second detection antibody coupled to a second label and binding to the second bound antibody may be used. The amount of bound first and bound second antibody and, thus, the amount of cleaved and total SNAP-25 can subsequently derived from the amount of determined first and second label. In an aspect, a first label envisaged herein may be an enzyme such as horseradish peroxidase. In another aspect, a second label envisaged herein may be an enzyme such as alkaline phosphatase. The labels can be used to catalyze a detectable conversion of non-fluorescent substrates into fluorescent products.

In yet another aspect of the method of the invention, assaying is carried out by determining neurotransmitter release, e.g., into the culture medium. The amount of released or non-released neurotransmitter can be determined by techniques described herein or elsewhere.

Advantageously, the methods contemplated by the present invention are based on non-animal resources, e.g., the hiPS cell derived neuronal cells, and, therefore, avoid animal testing. The hiPS cell derived neuronal cells, nevertheless, allow for testing of all biological activities of BoNTs required, e.g., (a) receptor binding, (b) internalization, (c) translocation across the endosomal membrane into the cytosol, and/or (d) endoproteolytic cleavage of proteins involved in synaptic vesicle membrane fusion. Accordingly, the methods can be used for safety or quality control measures as well as for the development of BoNTs with modified biological properties usually requiring, e.g., large scale screening approaches.

The present invention also relates to a method for determining the amount of biologically active BoNT in a preparation comprising biologically active BoNT, comprising the steps of: (a) contacting a hiPS cell derived neuronal cell with a sample of the said preparation; and (b) determining the amount of biologically active BoNT present in the preparation by assaying the sample for the biological activity of BoNT.

The invention also relates to the use of the hiPS cell derived neuronal cell for assaying BoNT activity in a composition as specified elsewhere herein.

In an aspect, the assaying encompasses determining the presence or absence of BoNT activity and/or biologically active BoNT. The qualitative assay for biologically active BoNT may be used, e.g., in applications aiming at risk assessment in order to prevent any harm caused by BoNTs, e.g., as safety control measure during the manufacturing process or during the pharmaceutical or cosmetic applications of BoNTs or for preventing criminal conduct based on BoNTs, such as bioterrorism.

In another aspect, the assaying encompasses determining the amount of BoNT activity and/or biologically active BoNT. The quantitative assay for biologically active BoNT may be used during the process for BoNT manufacture or for adjusting a proper dosage of biologically active BoNT for cosmetic or pharmaceutical applications. Accordingly, such an assay may also be useful as a means for quality control or for the formulation of proper pharmaceutical or cosmetic products.

The invention also relates to the use of the hiPS cell derived neuronal cell for determining the amount of biologically active BoNT in a preparation comprising said biologically active BoNT as specified elsewhere herein.

The references cited in this specification above are herewith incorporated by reference with respect to their entire disclosure content and the disclosure content specifically mentioned in this specification.

EXPERIMENTAL

The following examples are provided in order to demonstrate and further illustrate certain preferred embodiments and aspects of the present invention and are not to be construed as limiting the scope thereof.

Example 1

A. Methods

Neuronal cells: The human iPS derived neurons were supplied frozen by Cellular Dynamics Inc. (Madison, Wis.). Neurons were thawed according to Cellular Dynamics instructions, and live cells were counted by Trypan Blue exclusion assay. Cells were seeded at a density of 40,000 cells per well into 96-well dishes (TPP, MidSci) coated with 0.01% poly-L-ornithine (SIGMA) and 8.3 μg/$cm^2$ matrigel (BD Biosciences) unless otherwise indicated, and incubated in neuronal medium (Neurobasal supplemented with B27 and glutamax, all from Invitrogen and supplied by CDI) at 37° C., 5% $CO_2$ for the indicated maturation times. At 24 h after seeding, the medium was changed completely, and half of the medium was replaced every 2-3 days thereafter.

Primary rat spinal cord (RSC) cells were prepared as previously described (Pellett et al., 2007 and 2010), and seeded into matrigel-coated 96-well plates at a density of 75,000 cells per well.

Botulinum Neurotoxin:

Pure botulinum neurotoxin (BoNT) A, B, C and E (150 kDa) and BoNT/A complex were prepared from *C. botulinum* strains Hall A hyper, Okra B, Brazil C, and Beluga E as previously described (Malizio et al., (2000) *Methods Mol Biol* 145: 27-39; Prabakaran et al., (2001) *Toxicon* 39: 1515-1531), whereby BoNT/C purification was performed by the method of Malizio et al (2000) with the additional step of addition of 0.2 mg/ml of yeast RNA (SIGMA) to the culture before ammonium sulfate precipitation. The toxins were dissolved in phosphate buffered saline, pH 7.4 and 40% glycerol, and stored at −20° C. until use. Activity of the BoNT/A, /B, /C, /E and BoNT/A-complex preparations was determined by the mouse bioassay (Hatheway C L (1988), supra; Schantz E J & Kautter D A (1978) *J Assoc Off Anal Chem* 61: 96-99), and specific toxicity was $7\times10^7$ mouse $LD_{50}$ Units/mg (BoNT/A1), 7.7×107 $LD_{50}$ Units/mg (BoNT/A1 complex), $1\times10^8$ $LD_{50}$ Units/mg (BoNT/B), $1.1\times10^7$ $LD_{50}$ Units/mg (BoNT/C), and $7.6\times10^7$ $LD_{50}$ Units/mg (BoNT/E).

Neuronal Toxicity Assays:

For all neuronal toxicity assays, iPS neurons were exposed to serial dilutions of BoNT in 50 μl of neuronal medium as indicated unless otherwise indicated. Primary Rat Spinal Cord cells were used as control cells in some assays as indicated in the results. All samples were tested in a minimum of triplicate, and a negative control without toxin was always included. After the specified exposure time, the toxin solution was removed, and cells were lysed in 50 μl of 1×LDS sample buffer (Invitrogen). The cell lysates were analyzed by Western blot for SNAP-25, or VAMP2 cleavage as previously described (Pellett et al., (2007), supra; Pellett et al., (2010), supra). Cleaved and un-cleaved bands were quantified by densitometry using a Foto/Analyst FX system and TotalLab Quant software (Fotodyne). Data plots were prepared and $EC_{50}$s derived using PRISM software.

Matrix Selection:

To select the optimal surface matrix, the neurons were seeded onto seven different matrices. The matrices consisted of poly-D-lysine coated plates (BD biosciences) coated with 1.0 μg/$cm^2$ either laminin (PDL laminin) or 8.3 μg/$cm^2$ matrigel (PDL matrigel), plates coated with 0.01% poly-L-ornithine followed by coating with either 1.0 μg/$cm^2$ laminin (PLO laminin) or 8.3 μg/$cm^2$ matrigel (PLO matrigel), PLO-laminin coated plates purchased from BD Biosciences (PLO-laminin (BD)), PDL coated plates from BD Biosciences (PDL (BD)), or 0.01% PLO coated plates (PLO (CDI)). Neurons were allowed to mature for 14 days, and sensitivity to BoNT/A was determined by exposing neurons to serial dilutions of the toxin for 48 h. Some of the neurons were maintained for 6 weeks and tested again as above.

Receptor Expression Analysis:

For the receptor expression analysis, iPS neurons were plated onto 24-well plates at a density of 210,000 cells/well in a volume of 0.75 ml. The cells from 3 wells, respectively, were harvested at 4, 7, 10, 14, and 21 days after plating in 75 μl 1×LDS sample buffer (Invitrogen). Cell lysates were analyzed by Western blot for the expression of SV2A, B, and C isoforms, synaptotagmin I and II, SNAP-25, VAMP using an antibody that recognizes VAMP 2 or an antibody that recognizes VAMP 1, 2, and 3 isoforms, and syntaxin. Beta-actin was used as a loading control, and primary rat spinal cord cells were used as a positive control. The SV2C antibody (Janz R & Sudhof T C (1999) *Neuroscience* 94: 1279-1290) was generously provided by Roger Janz. All other antibodies were from Synaptic Systems (Göttingen, Germany). All antibodies recognize human proteins.

For mRNA analysis by real-time qPCR, three independent cultures of iPS neurons were maintained for the indicated times, respectively. Cells were lysed directly on the plate and RNA was purified using the RNeasy Mini Kit and the RNase-Free DNase Set (Qiagen, Valencia, Calif.). For a positive control, human adult total brain RNA was purchased (Agilent Technologies, Santa Clara, Calif.). For all samples, cDNA was generated using the SuperScript VILO cDNA Synthesis Kit (Life Technologies, Carlsbad, Calif.). Real-time qPCR amplification was performed on the LightCycler® 480 II (Roche, Basel, Switzerland) using the TaqMan® Gene Expression Master Mix and the following TaqMan Human Gene Expression Assays: SNAP25 (Hs00938962_m1); STX1A (Hs00270282_m1); STX1B (Hs01041315_m1); VAMP1 (Hs00249911_m1); VAMP2 (Hs00360269_m1); VAMP3 (Hs00922166_m1); SV2A (Hs00372069_m1); SV2B (Hs00208178_m1); SV2C (Hs00392676_m1); SYT1 (Hs00194572_m1); SYT2 (Hs00980604_m1) and the Human GAPDH Endogenous Control Primer Set (all from Life Technologies). Abs Quant/2$^{nd}$ Derivative analysis was performed on all samples and $C_p$ values were converted to relative fold change via normalization to the $C_p$ for endogenous GAPDH expression. Averages and standard deviation were calculated for each gene within the three biological replicates. Technical quadruplicate PCR reactions were performed for each gene.

Activity-Dependent BoNT/A1 Uptake Assays:

BoNT/A1 was diluted to a concentration of 55 or 275 U per 50 μl of cell-stimulation (Invitrogen custom Neurobasal medium containing 2.2 mM CaCl and 56 mM KCl, supplemented with B27 and glutamax) or neuronal mediums and added to CDI iPS neurons matured for 4 days and RSC cells. The cells were incubated with toxin for 1, 5, 10 and 15 min respectively. For the negative control, the respective medium without toxin was added to the cells. The toxin was removed and cells were immediately washed twice with 200 μl of neuronal medium followed by incubation in 200 μl of fresh neuronal medium for 24 h. Samples were collected in replicates of 4.

To determine the minimum required toxin concentration for activity-dependent uptake of BoNT/A1 within 5 min, the toxin was diluted to concentrations between 1.72 to 55 U per 50 μl of cell-stimulation medium. Four day matured iPS neurons were exposed to the toxin dilutions for 5 min, followed by toxin removal and two washes with neuronal medium and incubation in neuronal medium for 24 h. All dilutions were tested in replicates of 4.

Antibody-Protection Analysis:

BoNT/A1 specific antibodies were prepared according to Johnson et al., 1993. Inhibition of BoNT/A1 activity in iPS neurons by neutralizing antibodies was analyzed using two different methods. For the first assay, 55 U of BoNT/A1 was combined with serially diluted antibody in cell-stimulation medium and incubated for 1 h at 37° C. to allow for antibody-toxin interaction. Four day matured iPS neurons were exposed to the toxin-antibody mixture for 5 minutes, followed by removal of the toxin-antibody mixture and two washing steps with neuronal medium and incubation in neuronal medium for 24 h. For the second assay, 1.5 U of BoNT/A were combined with serial dilutions of antibody in neuronal medium and incubated at 37° C. for 1 h. The iPS neurons were exposed to the toxin-antibody mixtures for 24 h. Comparison with the mouse bioassay used serial dilution of the antibody pre-incubated with 5-10 U of BoNT/A1 for 1.5 h at ambient temperatures in a volume of 167 μL. The volume was adjusted to 500 microliters and injected into four mice per dilution.

B. Results

The iPS Neurons Express Receptors Important for BoNT Intoxication:

In order to determine whether the human iPS derived neurons can be used to detect BoNT activity, expression of the receptors and enzymatic targets necessary for BoNT cell entry and catalytic activity were analyzed by Western blot and quantitative PCR (qPCR), respectively (FIG. 1). The Western blot resulted in signals for SV2A, a faint band for SV2B, synaptotagmin 1, syntaxin, SNAP-25, VAMP2, and beta-actin, which did not change over a time period of 21 days after cell plating (FIG. 1A). While VAMP2 was detected with a VAMP2 specific antibody, an antibody that recognizes all three VAMP isoforms resulted in no signal, indicating that VAMP2 is the predominant VAMP isoform in iPS neurons. Primary rat spinal cord cell lysate was used as a positive control for antibody detection, and the different intensities in bands of iPS neurons versus RSC cells may be due to differential recognition by the antibody or to different expression levels. Analysis of mRNA levels of the same proteins by qPCR indicated expression of all proteins analyzed (FIG. 2B) including SV2B and C isoforms, synaptotagmin 2, and VAMP1 and 3, which were not detected by Western blot. However, the mRNA levels of those isoforms were at least 200-fold lower than those of the isoforms detected by Western blot (SV2A, synaptotagmin 1, and VAMP2). Thus, the qPCR data corroborate the Western blot data and indicate that the iPS neurons express primarily SV2A, synaptotagmin 1, and VAMP2 isoforms of these proteins, which is consistent with the neurons representing fore-brain neurons (Janz R & Sudhof T C (1999) Neuroscience 94: 1279-1290). Expression levels of all proteins did not change throughout the study period, indicating that the cells are fully matured at 4 days after plating and remain stable for at least 21 days.

The Surface Matrix does not Influence the Quality of the Cells for the BoNT/A1 Assay:

To determine if the plating matrix influenced the sensitivity to BoNT, neurons plated on seven different matrices were tested for BoNT/A1 sensitivity. The neurons attached to and matured on all matrices, forming an increasing network of axons and dendrites. Significant morphological differences were observed between the cells grown on plates with or without laminin or matrigel. The cells grown on PDL (BD Biosciences) laminin or matrigel plates or on PLO (Cellular Dynamics) laminin or matrigel plates grew mostly in a monolayer but formed some aggregates with long axons extending from them, primarily around the perimeter of the plates. In contrast, the cells grown on PLO or PDL plates remained in a single monolayer of cells with axons and dendrites extending between the networks of cells. The cells grown on PLO laminin (BD Biosciences) resembled cells grown on PLO or PDL plates.

Figure 2:
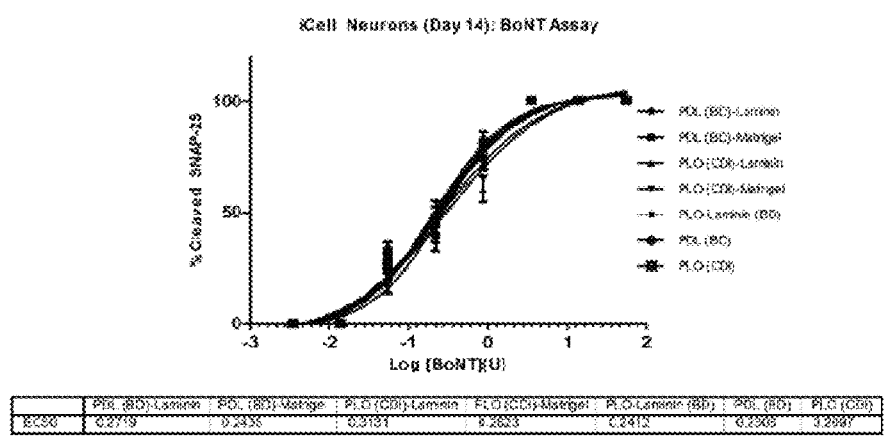
FIG. 2 shows a comparison of BoNT/A1 sensitivity of iPS neurons plated on 7 different substrates (indicated on right).
Figure 2:
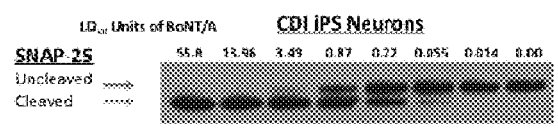

The neurons were exposed to serial dilutions of BoNT/A after 14 days of maturation, and Western blot analysis of cell lysates indicated that SNAP-25 cleavage was nearly identical for all substrates tested (FIG. 2). The limit of detection was 0.05 mouse $LD_{50}$ Units, and cleavage was complete between 1.75 and 3.5 U. The $EC_{50}$s ranged from 0.21 to 0.31.

These data indicate that the cells can be plated on any of the tested surface matrices for this assay. All following experiments were performed on PLO-matrigel coated plates. In order to reduce cell aggregation, TPP plates (MidSci) were used, which have a flatter surface area. This completely eliminated aggregation around the well perimeter.

Figure 3:
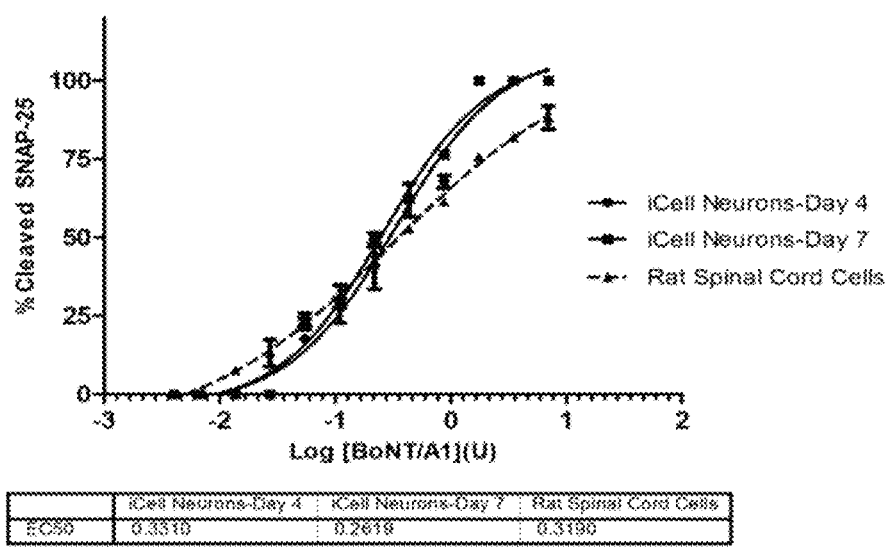
FIG. 3 shows BoNT/A1 sensitivity of iPS neurons and RSC cells.

A Cell Maturation Time of 4-14 Days Provides an Excellent and Sensitive BoNT/A1 Testing Platform:

In order to determine whether the cell maturation time affects BoNT sensitivity of iPS neurons, the cells were analyzed for BoNT/A1 sensitivity at 4 and 7 days after plating in parallel using the same toxin dilutions. Primary rat spinal cord cells (RSC cells) were also tested in parallel, to compare sensitivity of the iPS neurons to RSC cells, which are currently the most sensitive cells described for BoNT detection (Pellet et al., 2007, supra; Pellett et al., (2010) *J Pharmacol Toxicol Methods*). The resulting data consistently showed no statistically significant differences in sensitivity of the cells matured for 4 or 7 days, with $EC_{50}$s of ~0.3 U (FIG. 3). This is similar to the $EC_{50}$ observed above for day 14 cells (FIG. 2) and for RSC cells. The dose-response curve for the iPS neurons was significantly steeper than for RSC cells, and 100% cleavage was reached with 1.75 U, while 100% cleavage was not reached in RSC cells with the toxin concentrations used. This is likely due to the high purity of the iPS neurons. Thus, cells matured 4-14 days provide a reproducible and highly sensitive cell based model for BoNT/A1 detection and quantification. In addition, testing of four different iPS cell lots indicated no major difference in BoNT/A1 sensitivity.

Figure 4:
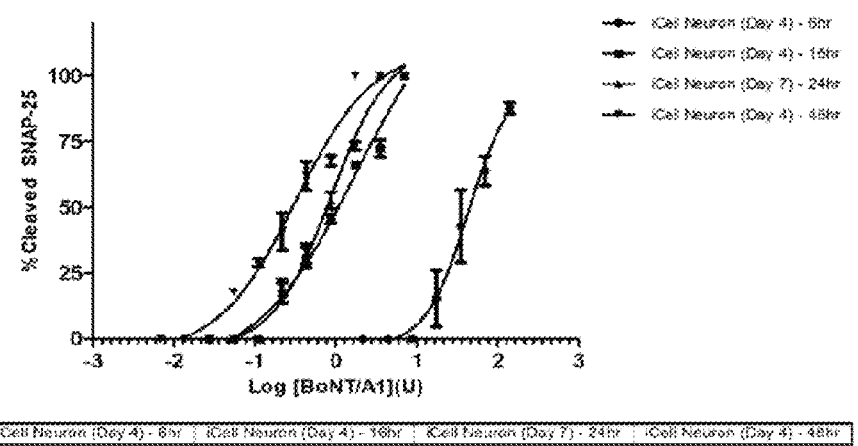
FIG. 4 shows time dependence of detecting BoNT/A1 activity in iPS neurons.

Sensitivity of iPS Neurons Increases with Longer Exposure Times:

The time dependence of BoNT detection in iPS neurons was examined by exposing the cells to serial BoNT/A1 dilutions and harvesting samples at 6, 16, 24, and 48 h after toxin addition. The resulting data consistently indicated that a 48 h exposure yielded highest sensitivity, with a ~3-fold increase compared to a 24 h assay and a ~6-fold increase compared to a 16 h assay (FIG. 4). A 6 h toxin exposure resulted in a ~130-fold decrease in sensitivity, with an $EC_{50}$ of about 40 Units.

The iPS Neurons have a Faster BoNT/A1 Uptake Rate than RSC Cells:

The BoNT/A1 uptake rate into iPS neurons compared to RSC cells was examined by exposing iPS neurons and RSC cells to 82 U of BoNT/A1 in parallel and assessing SNAP-25 cleavage at 2, 4, 6, 8, and 10 h. Two different media were used to differentiate between activity-dependent and independent toxin uptake, since neuronal activity has been reported to result in faster uptake of BoNTs (Keller et al., (2004), supra). The first medium was neuronal medium (NM), and the second was cell-stimulation medium (CSM), which is a modified version of the neuronal medium that contains 56 mM KCl and 2.2 mM $CaCl_2$ to chemically stimulate neuronal cell activity.

Figure 5:
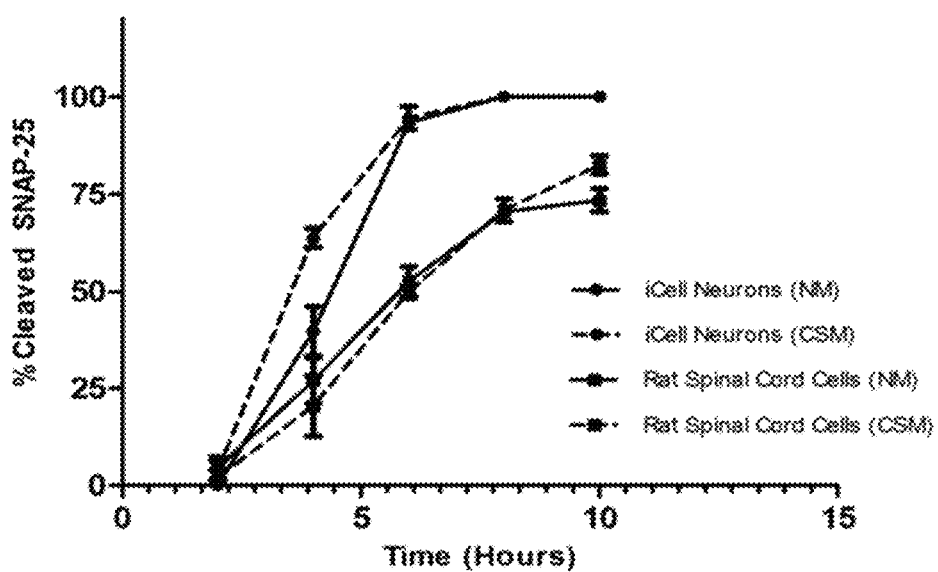
FIG. 5 shows the BoNT/A1 uptake rate of iPS neurons compared to RSC cells.

The iPS neurons resulted in significantly earlier and more complete SNAP-25 cleavage than the RSC cells. In iPS neurons, 100% of SNAP-25 cleavage was achieved at 8 h and 50% SNAP-25 cleavage at ~4 h (FIG. 5). The RSC cells, in contrast, reached only ~70-80% SNAP-25 cleavage after 10 h, and ~50% cleavage of SNAP-25 was observed at 6 h. No difference was observed between neuronal and cell-stimulation medium for either cell type, indicating that in the time frame tested neuronal activity does not affect BoNT uptake into the cells. These data indicate that the iPS neurons are significantly more sensitive to BoNT/A than RSC cells and take up the toxin at a faster rate, although this assay does not differentiate between faster toxin uptake and faster cleavage of SNAP-25.

Figure 6:
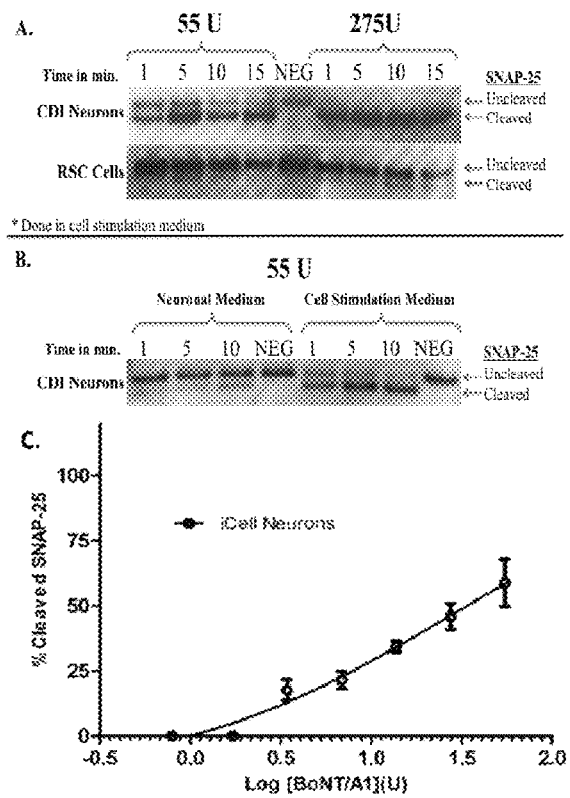
FIG. 6 shows activity-dependent BoNT/A1 uptake by neurons. A. iPS neurons and RSC cells were exposed to 55 U or 275 U of BoNT/A1 in cell-stimulation medium for 1, 5, 10 and 15 minutes, followed by toxin removal and 24 h incubation. B. iPS neurons were exposed to 55 U of BoNT/A1 in both neuronal and cell-stimulation mediums for 1, 5 and 10 min. C. Neurons were exposed to 1.7-55 U of BoNT/A1 for 5 min in cell-stimulation medium, washed twice with neuronal medium, and incubated for 24 h.

The iPS Neurons Take Up BoNT/A1 Significantly Faster than RSC Cells in an Activity-Dependent Assay:

In order to examine further whether iPS neurons take up BoNT in an activity-dependent fashion, 4 day matured iPS neurons and RSC cells were exposed to 55 and 275 U of BoNT/A1 in cell-stimulation medium, respectively. The cells were exposed to toxin for 1, 5, 10 or 15 min, followed by complete toxin removal and incubation in neuronal medium for 24 h to allow for SNAP-25 cleavage. Significant SNAP-25 cleavage was observed in iPS neurons as early as 1 min after exposure with 55 U of BoNT/A1 (FIG. 6A). After 5 min about 75% of SNAP-25 was cleaved, and there was no significant change with longer toxin exposures, indicating completed uptake within 5 minutes. Exposure to 275 U resulted in complete SNAP-25 cleavage at all exposure times tested (FIG. 6A). In contrast, exposure of RSC cells to 55 Units of BoNT/A1 did not result in significant SNAP-25 cleavage after exposure times of up to 15 min, and only about 30-40% of SNAP-25 was cleaved after an at least 10 min exposure to 275 U (FIG. 6A). This indicates that iPS neurons take up BoNT/A1 in an activity-dependent fashion, and that this uptake occurs markedly more efficiently and faster than in RSC cells.

In order to confirm that the fast uptake in iPS neurons is activity-dependent, the neurons were exposed to 55 U of BoNT/A for 1, 5, or 10 min in cell-stimulation medium or neuronal medium. There was significantly more SNAP-25 cleavage in the cells treated with cell-stimulation medium, with 50% cleavage of SNAP-25 observed after 1 min and 70% cleavage after 5 min (FIG. 6B). In neuronal medium, in contrast, only about 20% of SNAP-25 was cleaved after 10 minutes (FIG. 6B). This indicates that fast uptake of BoNT/A1 into iPS neurons is activity-dependent.

In order to determine concentration dependence of activity-dependent BoNT/A1 uptake by iPS neurons, the cells were exposed to 1.7-55 U of BoNT/A1 in cell-stimulation medium for 5 min. After toxin removal, cells were incubated for 24 h to allow for SNAP-25 cleavage to occur. A concentration dependent increase in SNAP-25 cleavage was observed with increasing toxin concentration, with 50% SNAP-25 cleavage occurring with about 30 U (FIG. 6C).

Figure 7:
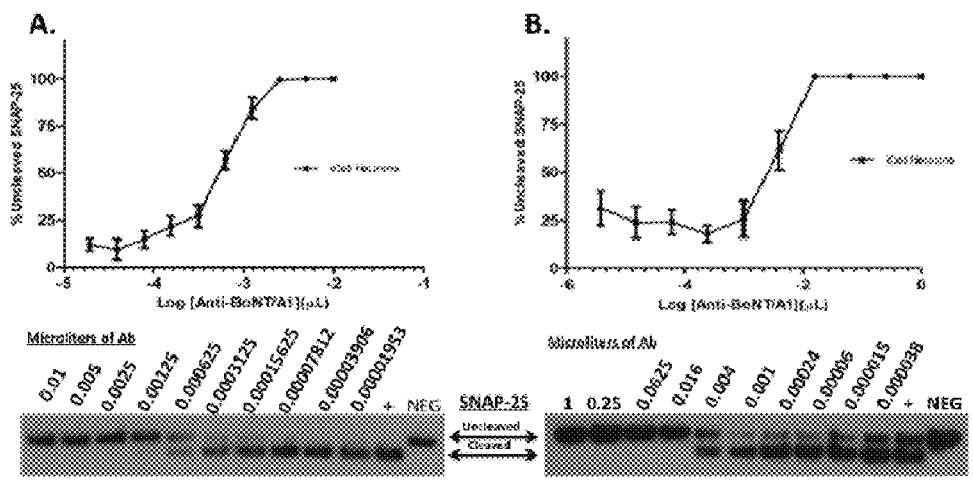
FIG. 7 shows Western blot and densitometry data of antibody protection assay in iPS neurons. A. iPS neurons were exposed to 1.5 U of toxin and antibody for 24 h. B. iPS neurons were exposed to 55 U of toxin-antibody mixture in cell-stimulation medium for 5 minutes, the mixture was removed, cells were washed twice, and incubated for 24 h.

BoNT/A1 Specific Antibodies Protect iPS Neurons from SNAP-25 Cleavage by BoNT/A1:

Specificity of the iPS BoNT assay was confirmed by an antibody protection assay using two different assay formats. In the first assay, the cells were exposed to the toxin antibody mixtures for 24 h, using the minimal amount of toxin required to achieve nearly complete SNAP-25 cleavage (1.5 Units). In the second assay, the cells were exposed to mixtures of 55 U BoNT/A and serially diluted antibody for 5 min in cell-stimulation medium, followed by toxin removal and incubation for 24 h. The first assay yielded significantly higher sensitivity in antibody detection. Neurons were fully protected from cleavage of SNAP-25 with as little as 0.0025 µl of antibody. Significant partial protection was observed down to 0.000625 µl of antibody (FIG. 7A). The same protection pattern was previously observed when the antibody was tested in RSC cells using 0.5 U of BoNT/A1 and a 48 h exposure. Testing the same antibody dilutions by mouse bioassay indicated an at least ~10 times greater sensitivity of the cell-based assays compared to the mouse bioassay as previous data have also indicated. +The RSC assay has been shown to be more sensitive in neutralizing antibody detection than the mouse bioassay (Pellett, S. 2007, supra). The second (activity-dependent) assay was about 10 times less sensitive, requiring 0.016 µl of antibody per 50 µl for full protection, and partial protection was observed with 0.004 µl (FIG. 7B).

This confirms specificity of this assay and indicates that the iPS neurons provide an excellent and highly sensitive assay for neutralizing antibody detection, and that a longer exposure with less toxin is more sensitive than an activity-dependent assay which requires more toxin but a shorter exposure time. The activity-dependent assay is useful for some purposes, such as screening of compounds or antitoxin that may be cytotoxic or need to be dissolved in solvents that may harm neurons over time.

Detection of BoNT/A1 Toxin in its Natural Complex is More Sensitive than Detection of Purified Toxin:

BoNTs are expressed in clostridia as a complex with several other proteins (nontoxic nongemagglutinin protein (NTNH) and hemagglutinins (HA) in the case of BoNT/A (reviewed in Johnson E A & Bradshaw M (2001) *Toxicon* 39: 1703-1722). The non-toxic complex proteins are believed to protect the toxin from the degradative pH of the gastrointestinal tract (Oguma et al., (2000) *Microbial Foodborne Diseases: Mechanisms of Pathogenesis and Toxin Synthesis* 273-293). The most commonly used medical preparations of BoNT/A (BOTOX® and Dysport® preparations) consist of the entire toxin complex, although newer formulations containing only the purified BoNT (Xeomin® preparation) have now been approved by the FDA. In order to determine whether BoNT/A1 in its natural complex is detected with equal sensitivity as pure BoNT/A1 in iPS neurons, the cells were exposed to equal amounts of BoNT/A1 complex or purified BoNT/A1 in parallel. The complex consists of about 24% BoNT/A1 and 76% other non-toxic associated proteins, as determined by densitometry (FIG. 8A). The purified BoNT/A1 preparation and BoNT/A1 complex had similar specific activities ($7 \times 10^7$ U/mg and $7.3 \times 10^7$ U/mg). In a direct comparison, significantly less of the toxin component of the complex was required to reach full SNAP-25 cleavage (FIG. 8B). This finding indicates that the non-toxic proteins of the complex increase BoNT/1A activity in this assay, possibly due to a protective effect in the neuronal medium.

The iPS Neurons are a Highly Sensitive Cell Model for Detection of BoNT Serotypes B, C, and E:

The BoNT receptor analyses indicated that iPS neurons express the SNARE proteins and receptors required for cell entry of all BoNT serotypes (FIG. 1). BoNT/A and /E cleave SNAP-25, BoNT/B cleaves VAMP, and BoNT/C cleaves SNAP-25 and syntaxin (Humeau et al., (2000) *Biochimie* 82: 427-446). To test the sensitivities of neurons to different serotypes, serial dilutions of BoNT/B, C, or E were added to iPS neurons or RSC cells for 48 h in parallel, and cell lysates were assayed via Western blot for the cleavage of their respective neuronal substrate. The iPS neurons consistently detected all BoNT serotypes with equal or greater sensitivity than RSC cells (FIG. 9). The $EC_{50}$ values for iPS neurons and RSC cells were 15.71 U and 29.22 U for BoNT/B (FIG. 9A), 0.4 U and 0.36 U for BoNT/C (FIG. 9B), and 1.79 U for BoNT/E in iPS neurons (FIG. 9C). An $EC_{50}$ value for BoNT/E in RSC cells could not be derived with the PRISM software, but is estimated to be similar to that of iPS neurons (FIG. 9C).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of assaying a *Clostridium botulinum* neurotoxin (BoNT) for activity, comprising the steps of:
   a) contacting a human induced pluripotent stem (hiPS) derived neuronal cell with a composition comprising a BoNT; and
   b) assaying the BoNT for biological activity.

2. The method of claim 1, wherein the BoNT is selected from the group consisting of BoNT serotype A, BoNT serotype B, BoNT serotype C, BoNT serotype E and modified variants thereof.

3. The method of claim 1, wherein the biological activity is selected from the group consisting of cleavage of SNAP-25, cleavage of VAMP2 and neurotransmitter release.

4. The method of claim 1, wherein the assay is qualitative.

5. The method of claim 1, wherein the assay is quantitative.

6. The method of claim 1, wherein the BoNT is purified.

7. The method of claim 1, wherein the BoNT is not in a complex.

8. The method of claim 1, wherein the BoNT is in a complex.

9. The method of claim 1, further comprising the step of contacting the BoNT with a test compound prior to contacting the hiPS derived neuronal cells.

10. The method of claim 9, wherein the test compound is an antibody.

11. The method of claim 10, wherein the antibody is a neutralizing antibody.

12. The method of claim 11, wherein the neutralizing antibody is in a sample selected from the group consisting of purified antibodies, serum and antitoxins.

13. A method of assaying a *Clostridium botulinum* neurotoxin (BoNT) for activity, comprising the steps of:
   (a) contacting a human induced pluripotent stem (hiPS) derived neuronal cell with a composition comprising i) a BoNT and ii) a neutralizing antibody; and
   (b) assaying the BoNT for biological activity.

14. The method of claim 13, wherein the BoNT is selected from the group consisting of BoNT serotype A, BoNT serotype B, BoNT serotype C, BoNT serotype E and modified variants thereof.

15. The method of claim 13, wherein the biological activity is selected from the group consisting of cleavage of SNAP-25, cleavage of VAMP2 and neurotransmitter release.

16. The method of claim 13, wherein the assay is qualitative.

17. The method of claim 13, wherein the assays is quantitative.

18. The method of claim 13, wherein the BoNT is purified.

19. The method of claim 13, wherein the BoNT is not in a complex.

20. The method of claim 13, wherein the BoNT is in a complex.

21. The method of claim 13, wherein the neutralizing antibody is in a sample selected from the group consisting of purified antibodies, serum and antitoxins.

22. A method for determining an amount of biologically active *Clostridium botulinum* neurotoxin (BoNT) in a preparation, comprising the steps of:
   (a) contacting a human induced pluripotent stem (hiPS) derived neuronal cell with a sample of a preparation comprising biologically active BoNT; and
   (b) determining the amount of biologically active BoNT present in the preparation by assaying the sample for the biological activity of BoNT.

* * * * *